United States Statutory Invention Registration [19]

[11] Reg. Number: H774

Miura et al. [43] Published: May 1, 1990

[54] R-ENANTIOMERS OF A $\Delta^2$-1,2,4-TRIAZOLIN-5-ONE DERIVATIVES

[75] Inventors: Yuzo Miura, Nishinomiya; Naoya Yamamoto, Osakasayami; Atsushi Tsushima, Kawachinagano; Mitsuru Kajioka, Sakai, all of Japan

[73] Assignee: Nihon Nohyaku Co., Ltd., Tokyo, Japan

[21] Appl. No.: 129,290

[22] Filed: Dec. 7, 1987

[30] Foreign Application Priority Data

Dec. 5, 1986 [JP] Japan ..... 61-290175

[51] Int. Cl.[5] ..... A01N 43/653; C07D 249/12

[52] U.S. Cl. ..... 71/92; 71/76; 548/263.2

[58] Field of Search ..... 548/263, 264, 265; 71/92, 76

[56] References Cited

U.S. PATENT DOCUMENTS

| | | | |
|---|---|---|---|
| 4,318,731 | 3/1982 | Kajioka et al. | 71/92 |
| 4,398,943 | 8/1983 | Kajioka et al. | 71/92 |
| 4,404,019 | 9/1983 | Uematsu et al. | 71/92 |
| 4,427,438 | 1/1984 | Nagano et al. | 71/92 |
| 4,452,981 | 6/1985 | Nagano et al. | 71/92 |

FOREIGN PATENT DOCUMENTS

| | | | |
|---|---|---|---|
| WO85/01637 | 4/1985 | Int'l Pat. Institute . | |
| WO85/04307 | 10/1985 | Int'l Pat. Institute . | |
| WO86/00072 | 1/1986 | Int'l Pat. Institute . | |
| WO86/02642 | 5/1986 | Int'l Pat. Institute . | |
| WO86/04481 | 8/1986 | Int'l Pat. Institute . | |
| 57-181069 | 11/1982 | Japan | 548/263 |
| 60-255780 | 12/1985 | Japan | 548/263 |
| 61-205265 | 9/1986 | Japan | 548/263 |
| 62-993688 | 8/1987 | Japan | 548/263 |
| 2162511 | 2/1986 | United Kingdom | 548/265 |

OTHER PUBLICATIONS

Nestler et al, "Synthesis and Herbicidal, etc.", *Z. Naturforsch,* 35b, pp. 366–371 (1980).

Funaki et al; Pesticide Chemistry—Human Welfare and the Environment; vol. 1, pp. 309–314; Structure–Activity Relationships of a New Fungicide S–33–0 and Its Derivatives.

Huebele et al; Pesticide Chemistry—Human Welfare and the Environment; vol. 1, pp. 233–242; The Fungcidal Activity of Acyl Anilines.

*Primary Examiner*—Matthew A. Thexton
*Assistant Examiner*—Chhaya Sayala
*Attorney, Agent, or Firm*—Cushman, Darby & Cushman

[57] ABSTRACT

R-Enantiomer of a $\Delta^2$-1,2,4-triazolin-5-one derivatives represented by general formula (I):

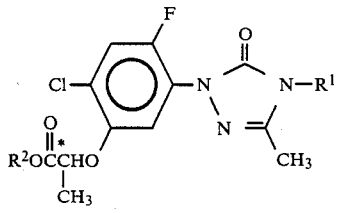

(I)

wherein $R^1$ represents a fluoroalkyl group having 1 to 2 carbon atoms and $R^2$ represents a hydrogen atom, a chloroalkyl group having 1 to 4 carbon atoms or an alkoxyalkoxyalkyl group having the total carbon atom numbers of 3 to 6, and a herbicidal composition containing the same.

19 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

R-ENANTIOMERS OF A $\Delta^2$-1,2,4-TRIAZOLIN-5-ONE DERIVATIVES

BACKGROUND OF THE INVENTION

Field of the Invention and Related Art Statement

The present invention relates to R-enantiomers of $\Delta^2$-1,2,4-triazolin-5-one derivatives represented by general formula (I):

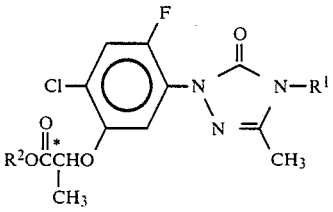

(I)

wherein $R^1$ represents a fluoroalkyl group having 1 to 2 carbon atoms and $R^2$ represents a hydrogen atom, a chloroalkyl group having 1 to 4 carbon atoms or an alkoxyalkoxyalkyl group having the total carbon atom numbers of 3 to 6, and herbicidal compositions comprising these derivatives as active components.

A part of the racemic modification of compounds represented by general formula (I) is known in Japanese Patent Application KOKAI (Laid-Open) Nos. 255780/85 and 205265/86 but optical isomers thereof are novel compounds which are not found in publications.

As the prior art of the present invention, compounds similar to those of the present invention are disclosed in U.S. Pat. Nos. 4,318,731, 4,404,019, 4,398,943, 4,427,438 and 4,452,981, Japanese Patent Application KOKAI (Laid-Open) Nos. 181069/82, 255780/85 and 205265/86, PCT Disclosure Nos. W085/01637, W085/04307, W086/00072, W086/02642 and W086/04481, etc. However, nothing is suggested or specifically disclosed with respect to optical isomers of the present invention. In addition, R-enantiomers of the $\Delta^2$-1,2,4-triazolin-5-one derivatives in accordance with the present invention exhibit a remarkable herbicidal effect which is unexpectedly superior to the known racemic compounds.

SUMMARY OF THE INVENTION

It is generally known that biological activities of optically active compounds having an asymmetric carbon atom are different between enantiomers. In view of difference in activity, toxicity, etc., attention is brought to optical isomers.

During the course of investigations on synthesis of racemic modification of the compounds represented by general formula (I), the present inventors have paid their attention to optical isomers. As a result of extensive investigations, the present invention has been accomplished.

R-Enantiomers of the compounds represented by general formula (I) according to the present invention are compounds having a marked herbicidal activity and selectivity to useful crops, as compared to their racemic modification.

A method for preparing the R-enantiomers of $\Delta^2$-1,2,4-triazolin-5-one derivatives represented by general formula (I) in accordance with the present invention is illustratively shown below.

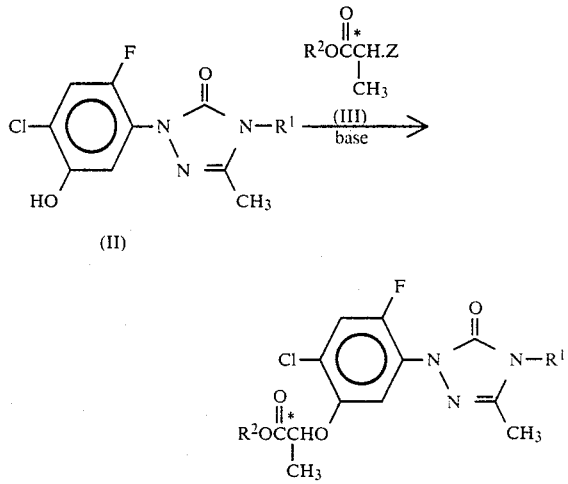

(II)

(I)

wherein $R^1$ and $R^2$ are the same as defined above and Z represents an alkylsulfonylkoxy group.

Namely, R-enantiomers of the compounds represented by general formula (I) can be obtained by reacting compounds represented by general formula (II) with S-enantiomers of compounds represented by general formula (III) in the presence of inert solvents.

DETAILED DESCRIPTION OF THE INVENTION

As the inert solvents which can be used in the reaction of the present invention, any solvent may be used as far as they do not markedly inhibit progress of the reaction of this kind. Examples of such inert solvents include aromatic hydrocarbons such as benzene, toluene, xylene, etc.; aliphatic hydrocarbons such as n-hexane, cyclohexane, etc.; alcohols such as methanol, ethanol, propanol, glycol, etc.; ketones such as acetone, methyl ethyl ketone, cyclohexanone, etc.; lower fatty acid esters such as ethyl acetate, etc.; ethers such as tetrahydrofuran (THF), dioxane, etc.; lower fatty acid amides such as dimethylformamide, dimethylacetamide, etc.; water, dimethylsulfoxide, etc.

These solvents can be used singly or as a mixture thereof.

As bases which can be used in the reaction, mention may be made of, for example, inorganic bases such as sodium carbonate, sodium hydride, sodium carbonate, sodium hydrogencarbonate, potassium hydrogencarbonate, sodium hydroxide, potassium hydroxide and alcoholates of alkali metals; organic bases such as pyridine, trimethylamine, triethylamine, diethylaniline, 1,8-diazabicyclo[5.4.0]-7-undecene, etc.

The reaction of the present invention can proceed at temperatures appropriately set in a range of, for example, 0° to 150° C.

The reaction of the compounds in respective reaction routes is an equimolar reaction but either compound may be added in a slightly excess amount.

The reaction time can be chosen from a range of 0.5 to 48 hours.

After completion of the reaction, the reaction product is treated in a conventional manner to give the In case that $R^2$ is a hydrogen atom in the compounds represented by general formula (I), the compounds can be obtained by hydrolysis or hydrogenation of the compounds represented by general formula (I) (except for the case in which $R^2$ is a hydrogen atom) in the presence of a catalyst.

Further the compounds represented by general formula (I) can also be prepared according to the equation shown below.

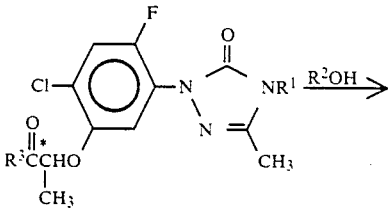

(I-a)

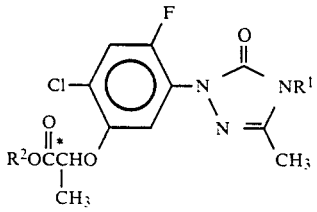

(I)

wherein $R^1$ and $R^2$ are the same as defined above and $R^3$ represents a hydroxy group or a halogen atom.

That is, the compounds represented by general formula (I) can also be prepared by reacting compounds represented by general formula (I-a) with the corresponding alcohol.

Representative examples of the compounds represented by general formula (I) are given below.

General formula (I)

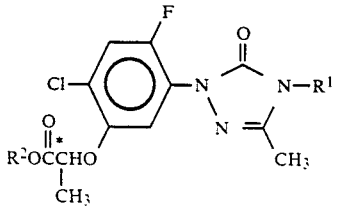

TABLE 1

| Compound No. | $R^1$ | $R^2$ | Physical Property | Optical Rotation c = 2.0 $[\alpha]_{D\,chloroform}$ |
|---|---|---|---|---|
| 1 | $CHF_2$ | H | m.p. 37~40° C. | $[\alpha]_D^{20.0}$ +21.5 |
| 2 | $CHF_2$ | $Cl(CH_2)_2$ | $n_D^{23.0}$ 1.5222 | |
| 3 | $CHF_2$ | $Cl(CH_2)_3$ | $n_D^{18.0}$ 1.5187 | $[\alpha]_D^{31.0}$ −31.3 |
| 4 | $CHF_2$ | $Cl(CH_2)_4$ | $n_D^{23.0}$ 1.5188 | $[\alpha]_D^{21.0}$ −31.3 |
| 5 | $CHF_2$ | $CH_3(OCH_2CH_2)_2$ | $n_D^{22.9}$ 1.5068 | $[\alpha]_D^{22.0}$ −25.6 |
| 6 | $CHF_2CF_2$ | H | m.p. 31~33° C. | $[\alpha]_D^{21.3}$ −21.5 |
| 7 | $CHF_2CF_2$ | $Cl(CH_2)_2$ | $n_D^{23.0}$ 1.5028 | $[\alpha]_D^{20.4}$ +21.3 |
| 8 | $CHF_2CF_2$ | $Cl(CH_2)_3$ | $n_D^{23.2}$ 1.4994 | $[\alpha]_D^{21.4}$ −32.5 |
| 9 | $CHF_2CF_2$ | $Cl(CH_2)_4$ | $n_D^{22.7}$ 1.5015 | $[\alpha]_D^{21.4}$ +28.8 |
| 10 | $CHF_2CF_2$ | $CH_3(OCH_2CH_2)_2$ | $n_D^{23.0}$ 1.4912 | $[\alpha]_D^{21.6}$ +21.5 |

The compounds represented by general formula (II) can be prepared by methods described in Japanese Patent Application KOKAI (Laid-Open) Nos. 255780/85 and 205265/86. More specifically, the compounds represented by general formula (II) can be synthesized by the reaction step as follows;

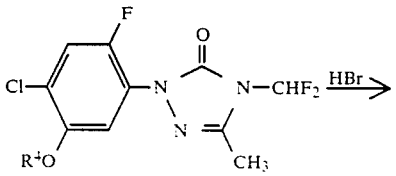

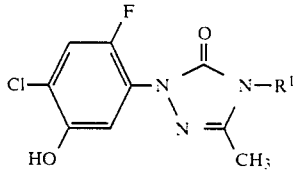

(II)

wherein $R^1$ is the same as defined above and $R^4$ represents a lower alkyl group.

In the above reaction, hydroiodic acid or an alkyl thiolate can be used in place of hydrobromic acid.

The compounds represented by general formula (III) can be prepared by methods described in U.S. Pat. No. 4,622,415.

The present invention will be described in more detail with reference to the examples below.

EXAMPLE 1

(R)-2-[2-Chloro-5-{4-(difluoromethyl)-3-methyl-5-oxo-$\Delta^2$-1,2,4-triazolin-1-yl}-4-fluorophenoxy]propionic acid [Compound No. 1]

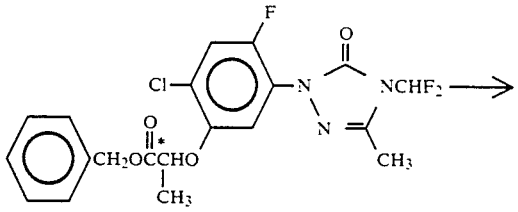

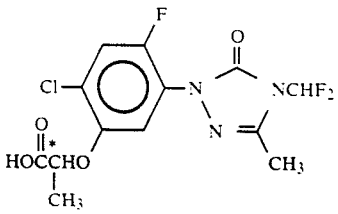

In 50 ml of tetrahydrofuran was dissolved 6.0 g (13.1 mmols) of benzyl-(R)-2-[2-chloro-5-{4-(difluoromethyl)-3-methyl-5-oxo-$\Delta^2$-1,2,4-triazolin-1-yl}-4-fluorophenoxy]propionate and, 2 or 3 drops of water and 1.0 g of 5% Pd-C were added to the solution. Hydrogen was passed through the mixture under normal pressure. After completion of the reaction, the catalyst was filtered off and the filtrate was concentrated to give the crude product. The crude product obtained was purified by column chromatography to give 1.53 g of the product as crystals. Yield, 33%. Physical properties: m.p. 37°-40° C., $[\alpha]_D^{20.0}+21.5$ (c=2.0, chloroform solution cell length of 20 cm)

Compound No. 6 was synthesized in a similar manner.

EXAMPLE 2

3-Chloropropyl (R)-2-12-chloro-{4-(difluoromethyl)-3-methyl-5-oxo-$\Delta^2$-1,2,4-triazolin-1-yl}-4-fluorophenoxy]propionate [Compound No. 3]

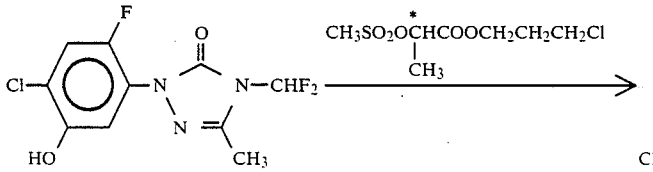

A mixture of 1.03 g (3.5 mmols) of 1-(4-chloro-2-fluoro-5-hydroxyphenyl)-3-methyl-4-(difluoromethyl)-$\Delta^2$-1,2,4-triazolin-5-one, 1.42 g (5.6 mmols) of 3-chloropropyl (S)-2-(methanesulfonyloxy)propionate and 0.58 g (4.2 mmols) of anhydrous potassium carbonate was refluxed in 60 ml of acetonitrile for 4 hours. After completion of the reaction, the reaction solution was allowed to cool to room temperature and poured onto ice water. After the product was extracted with ethyl acetate, the extract was washed with water and dried. The solvent for extraction was removed by distillation to give the crude product. The crude product obtained was purified by column chromatography to give 0.54 g of the product as oil. Yield, 36%. Physical properties: $n_D$ 1.5187 (18.0° C.), $[\alpha]^{31.0}$ +31.3 (c=2.0, chloroform solution, cell length of 20 cm)

Compound Nos. 2 and 4 were synthesized in a similar manner.

EXAMPLE 3

3-Chloropropyl (R)-2-[2-chloro-4-fluoro-5-{3-methyl-4-(1,1,2,2-tetrafluoroethyl)-5-oxo-$\Delta^2$-1,2,4-triazolin-1-yl}phenoxy]propionate [Compound No. 8]

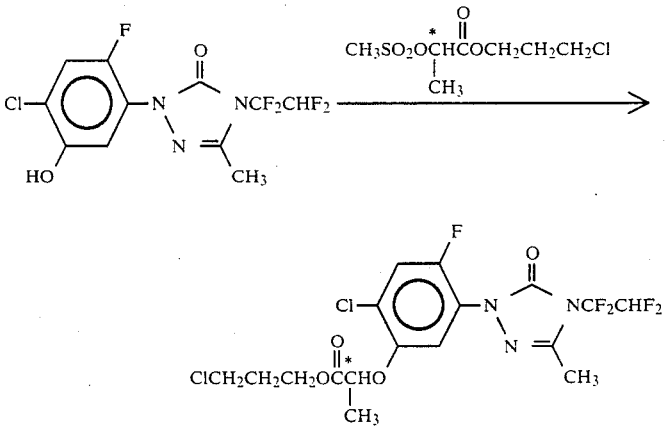

A mixture of 1.03 g (3.5 mmols) of 1-(4-chloro-2-fluoro-5-hydroxyphenyl)-3-methyl-4-(1,1,2,2-tetrafluoroethyl)-$\Delta^2$-1,2,4-triazolin-5-one, 1.42 g (5.6 mmols) of 3- 1 (S)-2-(methanesulfonyloxy)-propionate and 0.58 g (4.2 mmols) of anhydrous potassium carbonate was refluxed in 60 ml of acetonitrile for 4 hours. After completion of the reaction, the reaction solution was allowed to cool to room temperature and poured onto ice water. After the product was extracted with ethyl acetate, the extract was washed with water and dried. The solvent for extraction was removed by distillation to give the crude product. The crude product obtained was purified by column chromatography to give 0.67 g of the product as oil. Yield, 40%. Physical properties: $n_D$1.4994 (23.2° C., $[\alpha]^{21.4}+32.5$ (c=2.0, chloroform solution, cell length of 20 cm)

$^1$HNMR : $\delta_{TMS}$CDCl$_3$ (ppm)

1.70 (d. 3H), 2.10 (m. 2H), 2.45 (t. 3H),
3.50 (t. 2H), 4.30 (t. 2H), 4.75 (q. 1H),
6.85 (t. t. 1H), 7.00 (d. 1B), 7.25 (d. 1H).

Compound Nos. 7 and 9 were synthesized also in a similar manner.

EXAMPLE 4

2-(2-Methoxyethoxy)ethyl (R)-2-[2-chloro-4-fluoro-3-methyl-5-{4-(1,1,2,2-tetrafluoroethyl)-5-oxo-$\Delta^2$-1,2,4-triazolin-1-yl}-phenoxy]-propionate [Compound No. 10]

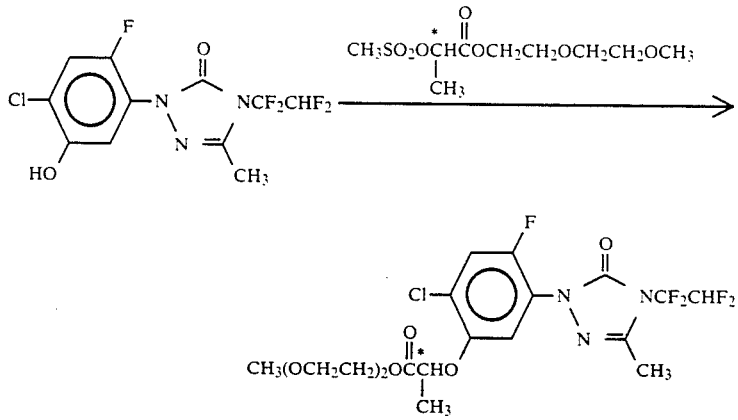

A mixture of 10.3 g (35 mmols) of 1-(4-chloro-2-fluoro-5-hydroxyphenyl)-3-methyl-4-(1,1,2,2-tetrafluoroethyl)-$\Delta^2$-1,2,4-triazolin-5-one, 15.0 g (56 mmols) of -(2-methoxyethoxy)ethyl (S)-2-(methanesulfonyloxy)propionate and 5.8 g (42 mmols) of anhydrous potassium carbonate was refluxed in 60 ml of acetonitrile for 4 hours. After completion of the reaction, the reaction solution was allowed to cool to room temperature and poured onto ice water. After the product was extracted with ethyl acetate, the extract was washed with water and dried. The solvent for extraction was removed by distillation to give the crude product. The crude product obtained was purified by column chromatography to give 11.8 g of the product as oil. Yield, 65%. Physical properties: $n_D$ 1.5068 (22.9° C.) $[\alpha]_D^{22.0}$ +21.5 (c=2.0, chloroform solution, cell length of 20 cm)

$^1$HNMR: $\delta_{TMS}^{CDCl_3}$ (ppm) 1.65 (d. 3H), 2.45 (t. 3H), 3.35 (s. 3H), 3.5–3.8 (m. 6H), 4.35 (m. 2H), 4.75 (q. 1H), 6.85 (t. t. 1H), 7.05 (d. 1H), 7.25 (d. 1H).

Compound No. 5 was synthesized also in a similar manner.

The R-enantiomers of $\Delta^2$1,2,4-triazolin-5-one derivatives represented by general formula (I) according to the present invention are capable of controlling annual and perennial weeds grown in paddy fields and orchards, such as wild oats (*Avena fatua L.*, an annual gramineous grass grown in plains, waste lands, and paddy fields), mugwort (*Artemisia princeps* Pamp., a perennial composite grass grown in mountain and paddy fields), large crabgrass (*Digitaria adscendcus* Henr., an annual gramineous grass which is a typical strongly injurious weed grown in paddy fields and orchards). Curly dock (*Rumex japonicus* Houtt., a perennial polygonaceous weed grown in paddy fields and on roadsides), umbrella sedge (*Cyperus iria* L., an annual cyperaceous weed grown in paddy fields and on roadsides), and Redroot pigweed (*Amaranthus varidis* L., an annual weed of Amaranthaceae family grown in vacent lands, roadsides and paddy fields), etc.

Since the compounds represented by general formula (I) described above exhibit an excellent controlling action against weeds in the prior and initial stages of emergence, they are particularly useful as herbicides for treating fields with the compounds before seeding (planting) crops in the fields, for example, soybeans, cottons, corns, etc. therein, after seeding (planting) these crops therein, treating fields at the growth stage of these crops therein, treating stalks and leaves before seeding (planting) these crops, and treating stalks and leaves at the growth stage of these crops. Further, they can also be used as a herbicide applying at initial and middle stage of rice for paddy fields and moreover, as a herbicide to control general weeds grown in, for example, reaped fields, temporarily non-cultivated fields, ridges between paddy fields, agricultural pathways, waterway, fields constructed for pasture, graveyards, parks, roads, playgrounds, unoccupied areas around buildings, reclaimed lands, railways, forests, etc. Herbicidal treatment of such areas is carried out most effectively and economically but not necessarily prior to the emergence of weeds.

For applying the compounds of the present invention as a herbicide, they are generally made up, according to the customary procedure for preparing agricultural chemicals, into a form convenient to use.

That is, the compounds described above are blended with suitable inert carriers and, if necessary, further with adjuvants, in a suitable ratio, and through dissolution, dispersion, suspension, mechanical mixing, impregnation, adsorption, or adhesion, a suitable form of preparation, e.g., suspension, emulsifiable concentrates, solution, wettable powders, dusts, granules, or tablets may be obtained.

The inert carriers to be used in the formulations may be either solids or liquids. As examples of the adaptable solid carriers, may be cited vegetable powders such as soybean flour, cereal flour, wood flour, bark flour, saw dust, powdered tobacco stalk, powdered walnut shell, bran, powdered cellulose, extraction residues of vegetables, etc.; fibrous materials such as paper, corrugated paperboard, waste cloth, etc.; synthetic polymers such as powdered synthetic resins, etc.; inorganic or mineral products such as clays (e.g., kaolin, bentonite, and acid clay), talcs (e.g., talc and pyrophillite), siliceous substances [e.g., diatomaceous earth, silica sand, mica, and "white carbon" (highly dispersed synthetic silicic acid, also called finely divided hydrated silica or hydrated silicic acid; some commercial products contain calcium silicate as major constituent)], activated carbon, powdered sulfur, pumice, calcined diatomaceous earth, ground brick, fly ash, sand, calcium carbonate, calcium phosphate, etc.; chemical fertilizers such as ammonium sulfate, ammonium nitrate, urea, ammonium chloride, etc.; and farmyard manure, etc. These materials are used singly or in combination with one another. The material usable as liquid carriers are selected from those which are solvents for the active compounds and those which are non-solvent but can disperse the active ingredients with the aid of adjuvants. For example, the following materials can be used singly or in combination with one another; water, alcohols (e.g., methanol, ethanol, isopropanol, butanol, ethylene glycol), ketones (e.g., acetone, methyl ethyl ketone, methyl isobutyl ketone, diisobutyl ketone, and cyclohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent napththa, and alkylnapthalenes), halohydrocarbons (e.g., dichloroethane, chlorinated benzenes, chloroform and carbon tetrachloride), esters (e.g., ethylacetate, dibutyl phthalate, diisopropyl phthalate, and dioctyl phthalate), acid amides (e.g., dimethylformamide, diethylformamide, and dimethylacetamide), nitriles (e.g., acetonitrile), dimethyl sulfoxide, etc.

The adjuvants, which are exemplified below, are used according to individual purposes. In some cases, they are used in combination with one another. In some other cases, no adjuvant is used at all. For the purpose of emulsification, dispersion, solubilization and/or wetting of the active ingredients, are used surface active agents, for example, polyoxyethylene alkylaryl ethers, polyoxyethylene alkyl ethers, polyoxyethylene higher fatty acid esters, polyoxyethylene resinates, polyoxyethylene sorbitan monooleate, polyoxyethylene sorbitan monooleate, alkylarylsulfonates, naphthalenesulfonic acid condensation products, ligninsulfonates, and higher alcohol sulfate esters, etc. For the purpose of stabilizing the dispersion, tackification, and/or agglomeration of the active ingredients, may be used, for example, casein, gelatin, starch, alginic acid, methylcellulose, carboxymethylcellulose, gum arabic, polyvinyl alcohol, turpentine oil, rice bran oil, bentonite, ligninsulfonates, etc.

For the purpose of improving the flow property of the solid composition, it is recommendable to use waxes, stearates, alkyl phosphates, etc.

As peptizers for a dispersible composition, it is also recommendable to use naphthalenesulfonic acid condensation products, polyphosphates, etc.

It is also possible to add a defoamer such as, for example, a silicone oil, etc.

The content of the active ingredient may be adjusted as occasion demands; for the preparation of powdered or granulated products, it is usually 0.5 to 20% by weight, and for the preparation of emulsifiable concentrates or wettable powder products, it is desirably 0.1 to 50% by weight.

For destroying various weeds, inhibiting their growth, or protecting useful plants from the injury caused by weeds, a weed-destroying dosage or a weed growth-inhibiting dosage of the herbicidal composition of the present invention is applied as such or after properly diluted with or suspended in water or in other suitable medium, to the soil or the foliage of weeds in the area where the emergence or growth of weeds is undesirable.

The amount of the herbicide of the present invention to be used depends on various factors such as, for example, the purpose of application, objective weeds, the emergence or growth state of weeds and crops, the emergence tendency of weeds, weather, environmental conditions, the form of the herbicidal composition, the mode of application, the type of the field to be treated, the time of application, etc.

In applying the herbicidal composition of the present invention alone as a selective herbicide, it is suitable to select the dosage of the compound from the dose of 10 to 500 g per 10 ares, as the active ingredient.

In the case of using the compound of the present invention as a herbicide for soybeans to be grown in upland fields, it is desired to select the dosage of the compounds of the present invention from the range of 0.1 to 100 g, as the active ingredient.

Considering that, in the combined use of herbicides, the optimum dosage thereof is often lower than that in the single use, the present herbicide may be used in an amount lower than the above, when it is used in combination with another sort of herbicide.

The present herbicide is especially valuable for the pre-emergence treatment and initial emergence stage treatment of fields. In order to expand both the range of controllable weed species and the period of time when effective applications are possible or to reduce the dosage, the present herbicides can be used in combination with other herbicides, and this usage is within the scope of this invention.

The following examples illustrate the herbicidal effects of the present compounds and the formulations of the present compounds, but the invention is not to be limited to these examples.

TEST EXAMPLE

Controlling effect on upland field weeds of pre-emergence stage

Polyethylene vats, 10 cm×20 cm×5 cm (depth), were filled with soil and seeded with oats, barnyard, large crabgrass, redroot pigweed, mugwort, Curly dock, umbrella sedge and cocklebur, respectively, which were all injurious weeds grown in crop fields, and seeds were covered with soil.

The soil was treated with each of the active ingredients formulated to a given concentration of liquid, by spraying. After 21 days, the herbicidal effect was evaluated by comparing the results with those on the untreated plot, respectively.

Criterion for judging herbicidal activity:

5 . . . 100% control of weed growth
4 . . . 90 to less than 100% control of weed growth
3 . . . 80 to less than 90% control of weed growth
2 . . . 70 to less than 80% control of weed growth
1 . . . less than 70% control of weed growth The results are shown in Table 2.

TABLE 2

| Compound No. | Amount of active ingredient applied (g/are) | Effect of pre-emergence treatment | | | | | | | |
|---|---|---|---|---|---|---|---|---|---|
| | | Oats | Barnyard grass | Large crabgrass | Redroot pigweed | Mugwort | Curly dock | Umbrella sedge | Cocklebur |
| 1 | 0.5 | 4 | 5 | 5 | 5 | 5 | 5 | 5 | 5 |

TABLE 2-continued

| Compound No. | Amount of active ingredient applied (g/are) | Effect of pre-emergence treatment | | | | | | | |
|---|---|---|---|---|---|---|---|---|---|
| | | Oats | Barnyard grass | Large crabgrass | Redroot pigweed | Mugwort | Curly dock | Umbrella sedge | Cocklebur |
| 2 | 0.5 | 4 | 4 | 5 | 5 | 5 | 5 | 5 | 4 |
| 3 | 0.5 | 4 | 4 | 5 | 5 | 5 | 5 | 5 | 4 |
| 4 | 0.5 | 3 | 4 | 5 | 5 | 5 | 5 | 5 | 3 |
| 5 | 0.5 | 3 | 4 | 4 | 5 | 5 | 5 | 5 | 4 |
| 6 | 0.5 | 4 | 4 | 5 | 5 | 5 | 4 | 5 | 3 |
| 7 | 0.5 | 5 | 5 | 5 | 5 | 5 | 5 | 5 | 5 |
| 8 | 0.5 | 5 | 5 | 5 | 5 | 5 | 5 | 5 | 5 |
| 9 | 0.5 | 4 | 5 | 5 | 5 | 5 | 5 | 5 | 5 |
| 10 | 0.5 | 4 | 5 | 5 | 5 | 5 | 5 | 5 | 5 |
| A | 0.5 | 2 | 3 | 4 | 5 | 4 | 4 | 5 | 4 |
| B | 0.5 | 3 | 3 | 4 | 5 | 5 | 4 | 5 | 4 |

Compound No. A is Compound No. 1 described in Japanese Patent Application KOKAI (Laid-Open) No. 86 and Compound No. B is Compound No. 2 described in Japanese Patent Application KOKAI (Laid-Open) No. 85, which were provided as control compounds. The structures of Compound No. A and Compound No. B are as follows;

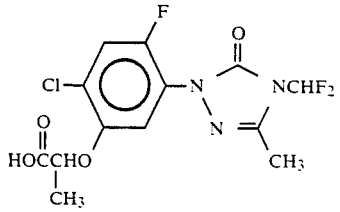

Compound A

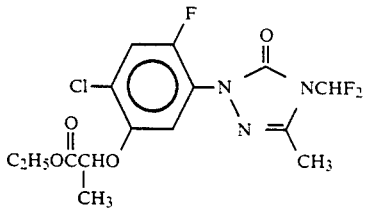

Compound B the following leaf stage. The soil was treated with each of the active ingredients formulated to a given concentration of liquid.

After 21 days, the herbicidal effect and the degree of crop injury were evaluated by comparing the results with those on the untreated plot.

Species of sample weed and its leaf stage and leaf stage of soybean:

| | |
|---|---|
| Oats | 2 leaf stage |
| Large crabgrass | 2 leaf stage |
| Redroot pigweed | 1 leaf stage |
| Mugwort | 1 leaf stage |
| Curly dock | 1 leaf stage |
| Umbrella sedge | 1 leaf stage |
| Cocklebur | 1 leaf stage |
| Soybean | First trifoliate stage |

Criterion for judging degree of chemical injury:

H . . . High (including withering)

M . . . Medium

L . . . Low

N . . . None

The criterion for judging the herbicidal activity is in accordance with Test Example 1. The results are shown in Table 3.

TABLE 3

| Compound No. | Amount of active ingredient applied (g/are) | Effect of post-emergence treatment | | | | | | | Phytotoxicity Soybean |
|---|---|---|---|---|---|---|---|---|---|
| | | Oats | Large crabgrass | Redroot pigweed | Mugwort | Curly dock | Umbrella sedge | Cocklebur | |
| 1 | 0.5 | 4 | 5 | 5 | 5 | 5 | 5 | 5 | N |
| 2 | 0.5 | 4 | 5 | 5 | 5 | 5 | 5 | 5 | L |
| 3 | 0.5 | 4 | 5 | 5 | 5 | 5 | 5 | 5 | L |
| 4 | 0.5 | 3 | 4 | 5 | 5 | 5 | 5 | 5 | N |
| 5 | 0.5 | 4 | 5 | 5 | 5 | 5 | 5 | 5 | L |
| 6 | 0.5 | 4 | 5 | 5 | 5 | 5 | 5 | 4 | N |
| 7 | 0.5 | 4 | 5 | 5 | 5 | 5 | 5 | 5 | N |
| 8 | 0.5 | 5 | 5 | 5 | 5 | 5 | 5 | 5 | N |
| 9 | 0.5 | 4 | 5 | 5 | 5 | 5 | 5 | 5 | N |
| 10 | 0.5 | 5 | 5 | 5 | 5 | 5 | 5 | 5 | N |
| A | 0.5 | 3 | 3 | 5 | 5 | 4 | 5 | 5 | N |
| B | 0.5 | 3 | 4 | 5 | 5 | 4 | 5 | 4 | N |

TEST EXAMPLE 2

Controlling effect on upland field weeds of post-emergence stage

Polyethylene vats, 10 cm×20 cm×5 cm (depth), were filled with soil and seeded with each of injurious weeds shown below and soybean seeds. The seeds were covered with soil and grown with each of the weeds of

TEST EXAMPLE 3

Effect on upland field weeds of post-emergence stage

Polyethylene vats, having 10×20×5 cm (depth) size, were filled with soil and seeded with the injurious weeds shown below and soybean seeds, respectively, and the seeds were covered with soil. The weeds and soybean were cultivated respectively to the following leaf stages and then treated with each active ingredient at a given dosage.

After 21 days, the herbicidal effect on the weeds and the degree of corp injury to the soybean were evaluated by comparing the results with those on the untreated plot.

| Species of test plant | Leaf stage |
|---|---|
| Barnyard grass | 2 |
| Velvetleaf | 2 |
| Jimson weed | 2 |
| Cocklebur | 1 |
| Soybean | First trifoliate stage |

The criteria for judging the herbicidal activity and crop injury were the same as in Test Examples 1 and 2, respectively. The results obtained are shown in Table 4.

TABLE 4

| Compound | Dosage g ai/ha | Crop/Weed S | B | V | J | C |
|---|---|---|---|---|---|---|
| Racemate of | 200 | 20 | 100 | 100 | 100 | 100 |
| Compound | 50 | 0 | 80 | 100 | 90 | 100 |
| No. 3 | 12.5 | 0 | 20 | 100 | 40 | 80 |
| Compound | 200 | 50 | 100 | 100 | 100 | 100 |
| No. 3 | 50 | 10 | 100 | 100 | 100 | 100 |
| (R-enantiom- | 12.5 | 0 | 60 | 100 | 80 | 100 |
| er) | | | | | | |
| Racemate of | 200 | 0 | 100 | 100 | 100 | 100 |
| Compound | 50 | 0 | 60 | 100 | 100 | 100 |
| No. 8 | 12.5 | 0 | 10 | 100 | 30 | 80 |
| Compound | 200 | 20 | 100 | 100 | 100 | 100 |
| No. 8 | 50 | 0 | 80 | 100 | 100 | 100 |
| (R-enantiom- | 12.5 | 0 | 50 | 100 | 70 | 100 |
| er) | | | | | | |
| Racemate of | 200 | 0 | 100 | 100 | 100 | 100 |
| Compound | 50 | 0 | 80 | 100 | 70 | 100 |
| No. 10 | 12.5 | 0 | 10 | 100 | 20 | 90 |
| Compound | 200 | 30 | 100 | 100 | 100 | 100 |
| No. 10 | 50 | 0 | 100 | 100 | 100 | 100 |
| (R-enantiom- | 12.5 | 0 | 70 | 100 | 80 | 100 |
| er) | | | | | | |

S = Soybean,
B = Barnyard grass,
V = Velvetleaf,
J = Jimson Weed,
C = Cocklebur

FORMULATION EXAMPLE 1

A wettable powder composition obtained by uniformly mixing and grinding the following components.

| | |
|---|---|
| Compound No. 1 | 50 parts |
| Mixture of clay and white carbon (clay is the major constituent) | 45 parts |
| Polyoxyethylene nonylphenyl ether | 5 parts |

FORMULATION EXAMPLE 2

A granule composition obtained by uniformly and grinding the following components, kneading the mixture with a suitable amount of water, and granulating the kneaded mixture.

| | |
|---|---|
| Compound No. 2 | 5 parts |
| Mixture of bentonite and clay | 90 parts |
| Calcium lignuninsulfonate | 5 parts |

FORMULATION EXAMPLE 3

An emulsifiable concentrate obtained by uniformly mixing the following components.

| | |
|---|---|
| Compound No. 3 | 50 parts |
| Xylene | 40 parts |
| Mixture of polyoxyethylene nonylphenyl ether and calcium alkylbenzenesulfonate | 10 parts |

FORMULATION EXAMPLE 4

A wettable powder composition obtained by uniformly mixing and grinding the following components.

| | |
|---|---|
| Compound No. 4 | 50 parts |
| Mixture of clay and white carbon (clay is the major constituent) | 45 parts |
| Polyoxyethylene nonylphenyl ether | 5 parts |

FORMULATION EXAMPLE 5

A granule composition obtained by uniformly mixing and grinding the following components, kneading the mixture with a suitable amount of water, and granulating the kneaded mixture.

| | |
|---|---|
| Compound No. 5 | 5 parts |
| Mixture of bentonite and clay | 90 parts |
| Calcium lignuninsulfonate | 5 parts |

FORMULATION EXAMPLE 6

An emulsifiable concentrate obtained by uniformly mixing the following components.

| | |
|---|---|
| Compound No. 6 | 50 parts |
| Xylene | 40 parts |
| Mixture of polyoxyethylene nonylphenyl ether and calcium alkylbenzenesulfonate | 10 parts |

FORMULATION EXAMPLE 7

A wettable powder composition obtained by uniformly mixing and grinding the following components.

| | |
|---|---|
| Compound No. 7 | 50 parts |
| Mixture of clay and white carbon (clay is the major constituent) | 45 parts |
| Polyoxyethylene nonylphenyl ether | 5 parts |

FORMULATION EXAMPLE 8

A granule composition obtained by uniformly mixing and grinding the following components, kneading the mixture with a suitable amount of water, and granulating the kneaded mixture.

| | |
|---|---|
| Compound No. 8 | 5 parts |
| Mixture of bentonite and clay | 90 parts |
| Calcium lignuninsulfonate | 5 parts |

FORMULATION EXAMPLE 9

An emulsifiable concentrate obtained by uniformly mixing the following components.

| | |
|---|---|
| Compound No. 10 | 50 parts |
| Xylene | 40 parts |
| Mixture of polyoxyethylene nonylphenyl ether and calcium alkylbenzenesulfonate | 10 parts |

What is claimed is:

1. An R-Enantiomer of a $\Delta^2$-1,2,4-triazolin-5-one compound represented by formula (I):

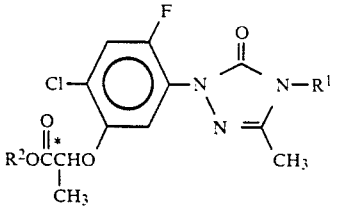

(I)

wherein $R^1$ represents a difluoromethyl group or a tetrafluoroethyl group and $R^2$ represents a chloropropyl group or a methoxyethoxyethyl group.

2. R-enantiomer according to claim 1 wherein $R^1$ is a difluoromethyl group.

3. R-Enantiomer according to claim 1 wherein $R^1$ is a tetrafluoroethyl group.

4. The R-enantiomer according to claims 2 or 3 wherein $R^2$ is a chloropropyl group.

5. The R-enantiomer according to claims 2 or 3 wherein $R^2$ is a methoxyethoxyethyl group.

6. R-Enantiomer according to claim 4 which is 3-chloropropyl (R)-2-[2-chloro-5-{4-(difluoromethyl)-3-methyl-5-oxo-$\Delta^2$-1,2,4-triazolin-1-yl}-4-fluorophenoxy]-propionate.

7. R-Enantiomer according to claim 4 which is 3-chloropropyl (R)-2-[2-chloro-4-fluoro-5-{3-methyl-4-(1,1,2,2-tetrafluoroethyl)-5-oxo-$\Delta^2$-1,2,4-triazolin-1-yl}phenxoy]propionate.

8. R-Enantiomer according to claim 5 which is 2-(2-methoxyethoxy)ethyl (R)-2-[2-chloro-5-{4-(difluoromethyl)-3-methyl-5-oxo-$\Delta^2$-1,2,4-triazolin-1-yl}-4-fluorophenoxy]propionate.

9. R-Enantiomer according to claim 5 which is 2-(2-methoxyethoxy)ethyl (R)-2-[2-chloro-4-fluoro-5-{3-methyl-4-(1,1,2,2-tetrafluoroethyl)-5-oxo-$\Delta^2$-1,2,4-triazolin-4-yl}phenoxy]propionate.

10. A herbicidal composition comprising as an active ingredient an R-enantiomer of a $\Delta^2$-1,2,4-triazolin-5-one compound represented by formula (I):

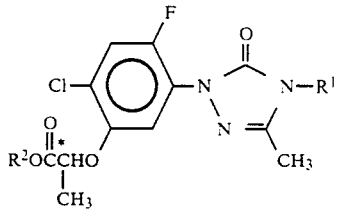

(I)

wherein $R^1$ represents a difluoromethyl group or a tetrafluoroethyl group and $R^2$ represents a chloropropyl group or a methoxyethoxyethyl group.

11. A herbicdal composition according to claim 10 wherein $R^1$ is a difluoromethyl group.

12. A herbicidal composition according to claim 10 wherein $R^1$ is a tetrafluoroethyl group.

13. A herbicidal composition according to claims 11 or 12 wherein $R^2$ is a chloropropyl group.

14. A herbicidal composition according to claims 11 or 12 wherein $R^2$ is a methoxyethoxyethyl group.

15. A herbicidal composition according to claim 11 or 12 which is a herbicidal composition for upland fields.

16. A herbicidal composition according to claim 15 which is 3-chloropropyl (R)-2-[2-chloro-5-{4-)difluoromethyl)-3-methyl-5-oxo-$\Delta^2$-1,2,4-triazolin-1-yl}-4-fluorophenoxy]propionate.

17. A herbicidal composition according to claim 15 which is 3-chloropropyl (R)-2-[2-chloro-4-5-{3-methyl-4-(1,1,2,2-tetrafluoroethyl)-5-oxo-$\Delta^2$-1,2,4-triazolin-1-yl}phenoxy]propionate.

18. A herbicidal composition according to claim 15 which is 2-(2-methoxyethoxy)ethyl (R)-2-[2-chloro-5-{4-(difluoromethyl)-3-methyl-5-oxo-$\Delta^2$-1,2,4-triazolin-1-yl}-4fluorophenoxy]propionate.

19. A herbicidal composition according to claim 15 which is 2-(2-methoxyethoxy)ethyl (R)-2-[2-chloro-4-fluoro-5-{3-methyl-4-(1,1,2,2-tetrafluoroehtyl)-5-oxo-$\Delta^2$-1,2,4-triazolin-1-yl}phenoxy]propionate.

* * * * *